US00PP21378P2

(12) United States Plant Patent
Scorza et al.

(10) Patent No.: US PP21,378 P2
(45) Date of Patent: Oct. 12, 2010

(54) PEACH TREE NAMED 'KV00398'

(50) Latin Name: ***Prunus persica* (L.) Batsch**
Varietal Denomination: KV00398

(75) Inventors: Ralph Scorza, Shepherdstown, WV (US); William R. Okie, Warner Robins, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/316,078

(22) Filed: Dec. 9, 2008

(51) Int. Cl.
*A01H 5/00* (2006.01)

(52) U.S. Cl. ..... Plt./198

(58) Field of Classification Search ..... Plt./198
See application file for complete search history.

*Primary Examiner*—Annette H Para
(74) *Attorney, Agent, or Firm*—John D. Fado; Evelyn M. Rabin

(57) ABSTRACT

A new and distinct variety of peach which is characterized by producing large, yellow, melting-flesh fruit with an excellent sweet, only mildly acidic dessert quality flavor. Fruit are melting flesh freestone with an 80% red over-color (blush) over a golden yellow undercolor and average 71 to 75 mm in diameter, ripening in early mid season.

2 Drawing Sheets

BACKGROUND OF THE NEW VARIETY

The present invention relates to a new and distinct variety of peach tree [*Prunus persica* (L.) Batsch] which is named 'KV00398'.

The new variety was originated at the Appalachian Fruit Research Station, Agricultural Research Service, U.S. Department of Agriculture in Kearneysville, W. Va. and was identified as KV00398. The present new variety, selected as KV00398 is a seedling selection of 'BY96P3480' which is a seedling of 'Blazeprince'×'BY90P2932'. 'Blazeprince' is a seedling resulting from 2 generations of open pollination of 'O'Henry' peach. BY90P2932 is a seedling of open pollination of BY87P1865 which in turn was a seedling of open pollination of BY84P1722 which was a seedling of (Flavortop×Fla. WL-1).

It was selected in 2003 from a group of 41 seedlings of the before said parent. It was vegetatively propagated by bud-grafting on to standard rootstock. The tree was propagated by a commercial nursery in Pennsylvania. Propagated trees were grown at the USDA-ARS-Appalachian Fruit Research Station and evaluated for trueness to type at that location in proximity to the original tree that was the source of propagative material. Testing for 5 years has shown that said variety maintains high fruit quality, large fruit size, a sweet and mild acidic flavor, and productivity. No aberrant types have appeared.

KV00398 is diploid, self-fertile and is cross compatible as a male or female parent with other peach varieties. No pollination incompatibilities have been noted.

This new variety is distinct from its parent in its combination of large size fruit, high fruit quality, sweet mildly acidic fruit, with an early mid-season time of ripening.

The fruit of this variety are melting flesh, dessert type. This variety is distinct from other peach cultivars in its combination of four distinct characteristics: (1) large size fruit, (2) yellow, melting-flesh fruit, (3) a distinct sweet, mildly acidic flavor, and (4) an outer appearance of 80% red blush over a golden yellow ground color. Flesh is yellow, flavorful sweet and only mildly acidic. They remain firm until full-ripe. Fruit have yellow ground color with red blush that covers approximately 80% of the fruit surface at maturity. Fruit size at harvest ranges from averages 70-80 mm in diameter with an average weight of 220 g. Fruit are sweet and flavorful with a mild acidity. Brix of firm-ripe fruit averages approximately 10° but can range from 9-12 depending on date of harvest and environment. Fruit maintain firmness on the tree and in storage at levels comparable to commercial peach cultivars.

SUMMARY OF THE INVENTION

A peach tree producing large yellow, melting-flesh fruit with a distinct sweet, mildly acidic flavor, of large size with approximately 80% red blush over a golden yellow ground color.

BRIEF DESCRIPTION OF THE DRAWINGS

FIG. 1 is a photograph of the fruit of the Fruit of 'KV00398' peach in full color showing the ripe fruit viewed in profile and sectioned in half from end to end, with one-half of the fruit shown with the stone in place in the flesh.

FIG. 2 is a full color photograph of a representative stem of flowers of the KV00398 peach at "balloon" stage.

The figures show photographs in color as accurate as reasonably possible to attain in color photographic reproductions of this type.

DETAILED DESCRIPTION OF THE NEW VARIETY

The following is a detailed description of the botanical and pomological characteristics of the subject peach. Color data are presented in Royal Horticultural Society (R.H.S.) Colour Chart designations. Where dimensions, sizes, color, and other characteristics are given, it is to be understood that such characteristics are approximations of averages set forth as accurately as practicable.

Age and growing conditions of plant observed and reported herein are from specimens grown at Kearneysville, W. Va. Data was taken from a 8 year old tree growing on its own roots growing at the USDA-ARS Appalachian Fruit Research Station—GPS coordinates 39° 21' 03" N, 77° 52' 53" W. The tree was planted in a field that received 40 lbs of nitrogen per acre. Field evaluations under a normal program of disease and pest control (see 2010 Spray Bulletin for Commercial Tree Fruit Growers, D.G. Pfeiffer et al. Virginia Cooperative Extension Publication 456-419 [Retrieved from the Internet: www.ext.vt.edu]) show no marked susceptibility to pathogens or insects when compared with peach varieties adapted to the eastern U.S. such as 'Bounty', 'Sweet-N-Up', and 'Sentry'. Measurements below are for the tree of the size and location as indicated above.

Tree:

*Size.*—Tree height: 3.7 m; tree width: 4.95×5.34 m.
*Vigor.*—Vigorous.
*Growth.*—Spreading.
*Density.*—Medium dense.
*Productivity.*—Productive.
*Bearing.*—Regular.

Trunk:

*Size.*—Trunk diameter 10 cm above ground: 21.3 cm.
*Color.*—Grey group RHS 201.
*Bark.*—Lenticel color: greyed orange N172A to greyed orange 169B. Lenticel size: 4.5 mm×2.02 mm.

Branches:

*Size.*—Average scaffold diameter at the point of attachment to trunk: 4.7 cm; average scaffold length: 214 cm.
*Texture.*—Smooth to medium rough, varies with maturity.
*Color.*—Greyed group RHS 201D.

Leaves:

*Size.*—Medium; average length 17 cm, average width 3.4 cm.
*Texture.*—Smooth.
*Thickness.*—Medium.
*Margin.*—Crenate.
*Form.*—Lanceolate, with an acuminate apex and an attenuate base.
*Petiole.*—Medium length; medium thickness.
*Glands.*—Reniform; 4 to 8 per leaf; average 1.3×0.72 mm RHS 154B to RHS 153D.
*Color.*—Upper surface — green RHS 137A; lower surface — green RHS 138A.

Flowers:

*Flower type.*—"Showy".
*Petal size.*—Length — 15 mm. Width at widest point — 14 mm. Width at base — 0.99 mm.
*Bloom period.*—Variable depending on weather, late March to mid-April in Eastern Panhandle of West Virginia.
*Color.*—At "balloon" stage Red Purple Group RHS 62C.
*Pollen.*—Present, color Yellow group RHS 9B.
*Anther number.*—42.
*Sepal color.*—Abaxial — green group 134C; adaxial — greyed purple 187C.
*Sepals.*—Abaxial pubescent, adaxial glaborous.

Fruit:

*Maturity when described.*—Shipping ripe to eating ripe.
*Average date of harvest.*—Early August in Kearneysville, W. Va.
*Size.*—Large; diameter axially averages 76 millimeters, ranging from 70 to 80 mm with a normal crop load.

Flesh:

*Ripens.*—Evenly.
*Texture.*—Firm.
*Fibers.*—Small, few, tender.
*Juice.*—Moderate.
*Aroma.*—Moderate.
*Flavor.*—Very good, sweet, mildly acidic.
*Eating quality.*—Excellent, only mildly acidic; average brix of 9 to 12° depending upon date of harvest and environmental conditions.
*Color.*—Yellow-orange RHS 16A to 16B; pit cavity red group RHS 45C.

Skin:

*Thickness.*—Medium.
*Tendency to crack.*—None.
*Down.*—Short in length.
*Color.*—Ground color yellow-orange RHS 16B with 70 to 80% of the surface orange-red RHS 34A with the darkest, sun exposed areas greyed-purple RHS 187A.
*Use.*—Dessert.
*Market.*—Local and long distance.

Stone:

*Type.*—Freestone.
*Size.*—Medium; average length 34 millimeters, average width 25 mm, average thickness 19 mm.
*Form.*—Obovate.
*Tendency to split.*—Low.
*Color.*—Greyed-orange RHS 177B to 177C with areas of RHS 184A and 183B.

We claim:

1. A new and distinct variety of peach tree producing fruit substantially as illustrated and described.

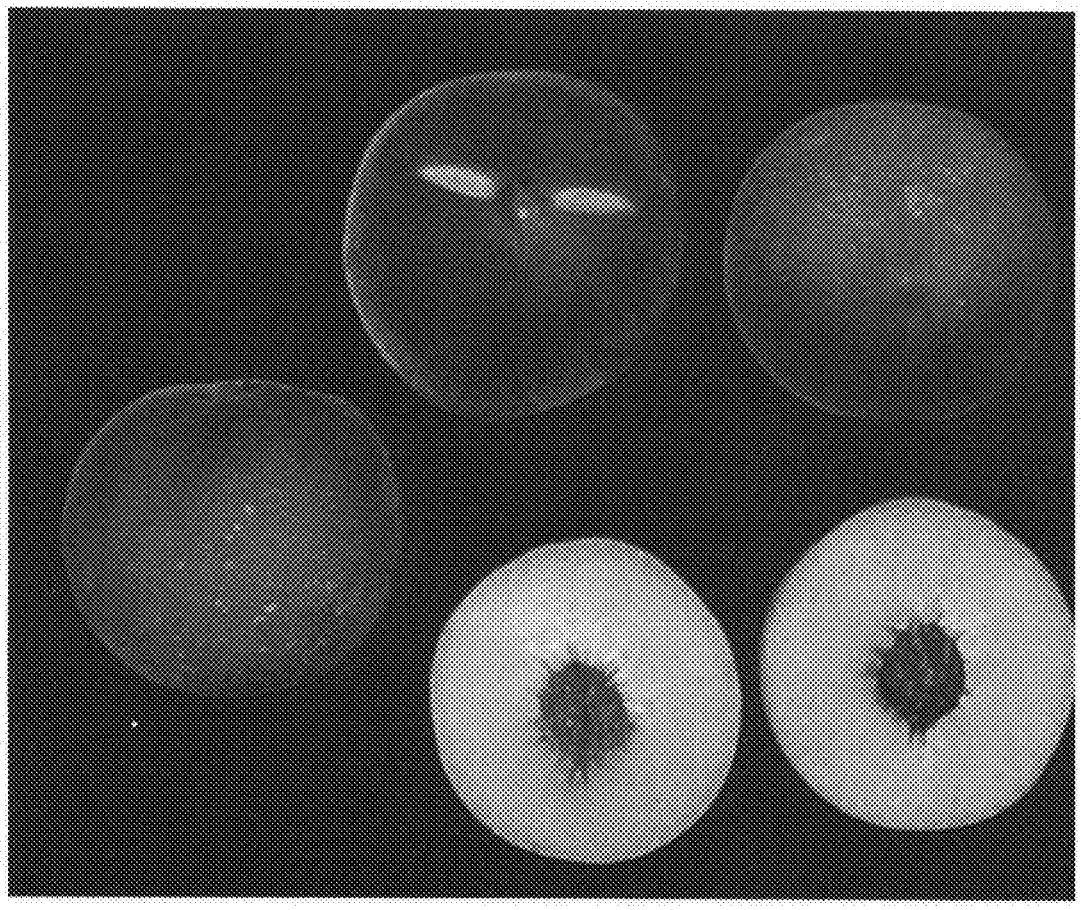

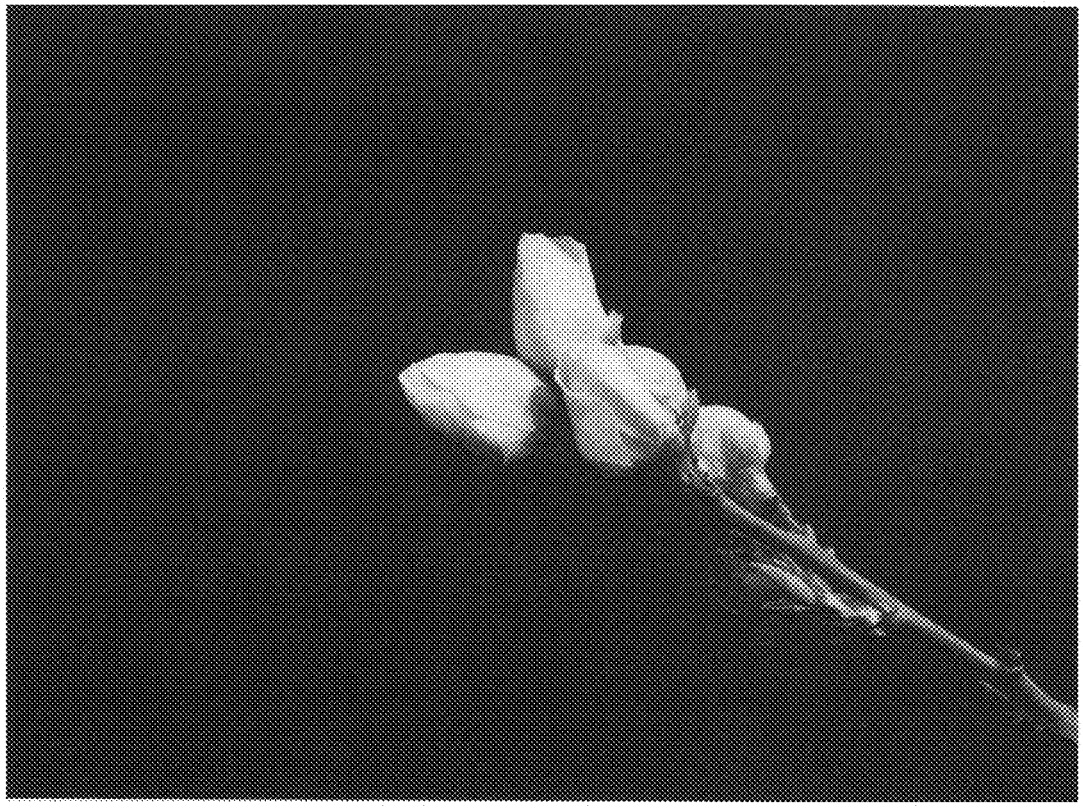

* * * * *